(12) United States Patent
Takeuchi

(10) Patent No.: US 8,241,215 B2
(45) Date of Patent: *Aug. 14, 2012

(54) ULTRASONIC DIAGNOSIS APPARATUS AND METHOD PROVIDING NAVIGATION INFORMATION FOR POSITIONING AN ULTRASONIC PROBE

(75) Inventor: Takashi Takeuchi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 165 days.

This patent is subject to a terminal disclaimer.

(21) Appl. No.: 11/311,484

(22) Filed: Dec. 20, 2005

(65) Prior Publication Data

US 2006/0100521 A1 May 11, 2006

Related U.S. Application Data

(62) Division of application No. 10/459,560, filed on Jun. 12, 2003, now Pat. No. 7,074,185.

(30) Foreign Application Priority Data

Jun. 12, 2002 (JP) ................................. 2002-171367

(51) Int. Cl.
A61B 8/08 (2006.01)
(52) U.S. Cl. .................. 600/440; 600/411; 382/128
(58) Field of Classification Search .............. 600/411, 600/440, 443, 427; 382/128
See application file for complete search history.

(56) References Cited

U.S. PATENT DOCUMENTS

| 4,237,902 A | 12/1980 | Okazaki |
| 4,444,197 A | 4/1984 | Koyano et al. |
| 6,014,580 A | 1/2000 | Blume et al. |
| 6,390,982 B1 * | 5/2002 | Bova et al. ............ 600/443 |

FOREIGN PATENT DOCUMENTS

| JP | 60-199439 | 10/1985 |
| JP | 5-300907 | 11/1993 |
| JP | 9-024035 | 1/1997 |
| JP | 10-151131 | 6/1998 |
| JP | 11-47133 | 2/1999 |
| JP | 11-151246 | 6/1999 |
| JP | 2000-139905 | 5/2000 |
| JP | 2000-217815 | 8/2000 |
| JP | 2000-217845 | 8/2000 |
| JP | 2001-29324 | 2/2001 |
| JP | 2001-276061 | 10/2001 |

OTHER PUBLICATIONS

Jason W. Trobaugh et al., Frameless Stereotactic Ultrasonography: Method and Applications, Computerized Medial Imaging and Graphics, Jul. 1994, vol. 18, No. 4, pp. 235-246.
Japanese Notice of Reasons for Rejection and English Translation for Application No. 2007-312820, mailed Feb. 16, 2011.

* cited by examiner

Primary Examiner — Parikha Mehta
(74) Attorney, Agent, or Firm — Oblon, Spivak, McClelland, Maier & Neustadt, L.L.P.

(57) ABSTRACT

A pre-acquired reference image, a currently picked-up ultrasonic image, and position information indicating a relation between a position of the ultrasonic probe when the reference image was picked-up and a current position of the ultrasonic probe are displayed on a display portion as navigation information. Also, when the following diagnosis image is to be acquired, probe movement information, specifying a position or the like to which the ultrasonic probe has to be moved, is displayed on the display portion as the navigation information.

20 Claims, 8 Drawing Sheets

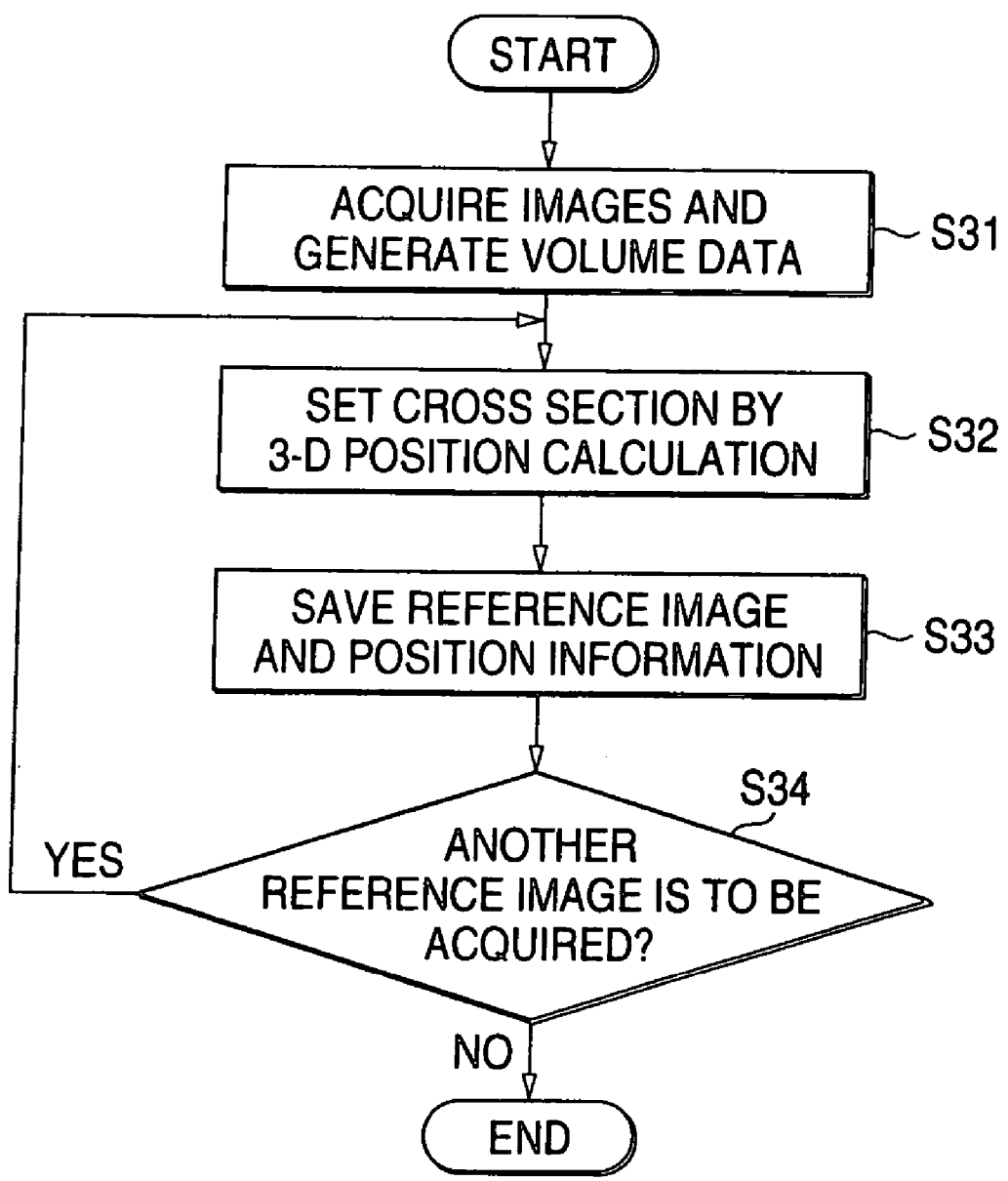

ULTRASONIC DIAGNOSIS APPARATUS AND METHOD PROVIDING NAVIGATION INFORMATION FOR POSITIONING AN ULTRASONIC PROBE

CROSS-REFERENCES TO RELATED APPLICATIONS

This application is a divisional of and claims the benefit of priority from allowed U.S. patent application Ser. No. 10/459,560 filed on Jun. 12, 2003, which claims the benefit of priority from Japanese Patent Application No. 2002-171367, filed on Jun. 12, 2002, the entire contents of all of which are incorporated herein by reference.

This application is based upon and claims the benefit of priority from the prior Japanese Patent Application No. 2002-171367, filed Jun. 12, 2002, the entire contents of which are incorporated herein by reference.

BACKGROUND OF THE INVENTION

1. Field of the Invention

The present invention relates to an ultrasonic diagnosis apparatus, an ultrasonic probe, and an ultrasonic imaging assisting method for use in, for example, medical care.

2. Description of the Related Art

An ultrasonic imaging diagnosis apparatus displays a tomographic image of tissue through a non-invasive examination method using ultrasound. The ultrasonic imaging diagnosis apparatus is quite useful at clinics in that, for example, beat pulsation of the heart or motions of a fetus can be displayed in real time through a manipulation as simple as placing an ultrasonic probe to the body surface. Also, because no X-rays or the like are used, a screening can be performed repetitively without concern for exposure. Further, it can be moved to a bedside for a screening to be conducted owing to its small system size in comparison with other diagnosis equipment for X-ray imaging, CT imaging, MRI, etc., and a further down-sized ultrasonic diagnosis apparatus has been under development.

Incidentally, the use of medical equipment is limited to specialized physicians or technicians due to a high skill and expert knowledge needed for manipulations. However, technical advancement in recent years has been improving medical equipment to the extent that it can be manipulated by non-specialized or less experienced physicians or technicians. In particular, because of the foregoing characteristics, the ultrasonic diagnosis apparatus is thought to be manipulated by a patient for himself in remote medical care, home medical care, etc. in the near feature.

However, in order to pick up a more suitable diagnosis image with a conventional ultrasonic diagnosis apparatus, the ability to read an ultrasonic image, the ability to see an ultrasonic image anatomically, etc. are required. This not only makes it difficult for non-specialized or less experienced physicians or technicians or a patient to manipulate the ultrasonic diagnosis apparatus, but also makes it almost impossible to pick up a suitable diagnosis image.

BRIEF SUMMARY OF THE-INVENTION

The invention was devised in view of the foregoing, and therefore, has an object to provide an ultrasonic diagnosis apparatus, an ultrasonic probe, and an ultrasonic imaging assisting method that make manipulations easier and adequate for non-specialized or less experienced physicians or technicians, etc.

The invention may provide an ultrasonic diagnosis apparatus, which includes: an ultrasonic probe that transmits ultrasound to a subject based on a driving signal and receives a reflection wave from the subject; a driving signal generator that supplies the ultrasonic probe with the driving signal; an image generator that generates a pick-up image based on the received reflection wave; a position detector that detects a position of the ultrasonic probe; a memory that stores a reference image acquired in past times and a reference position specifying a position of the ultrasonic probe in relation to the reference image; a navigation information generating unit that generates navigation information used to assist a manipulation of acquiring an ultrasonic image identical or similar to the reference image, based on the reference image, the reference position, the pick-up image, and a position of the ultrasonic probe in an instant of receiving ultrasound pertaining to the pick-up image; and an output unit that outputs the navigation information.

Also, the invention may provide an ultrasonic probe connected to an ultrasonic diagnosis apparatus and used to transmit ultrasound to a subject and receive a reflection wave from the subject. The ultrasonic probe includes a display device that displays, under control of the ultrasonic diagnosis apparatus, at least one of a direction in and a distance over which the ultrasonic probe has to be moved to acquire a desired ultrasonic image.

Further, the invention may provide an ultrasonic imaging assisting method, which includes: generating a pick-up image by scanning an interior of a subject with ultrasound with the use of an ultrasonic probe; detecting a position of the ultrasonic probe; generating navigation information used to assist a manipulation of acquiring an ultrasonic image identical or similar to a reference image acquired in past times, based on the reference image, a reference position specifying a position of the ultrasonic probe in relation to the reference image, the pick-up image, and a position of the ultrasonic probe in an instant of receiving ultrasound pertaining to the pick-up image; and outputting the navigation information.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is a flowchart used to explain operations of a navigation system according to a third embodiment.

DETAILED DESCRIPTION OF THE INVENTION

Figure 1:
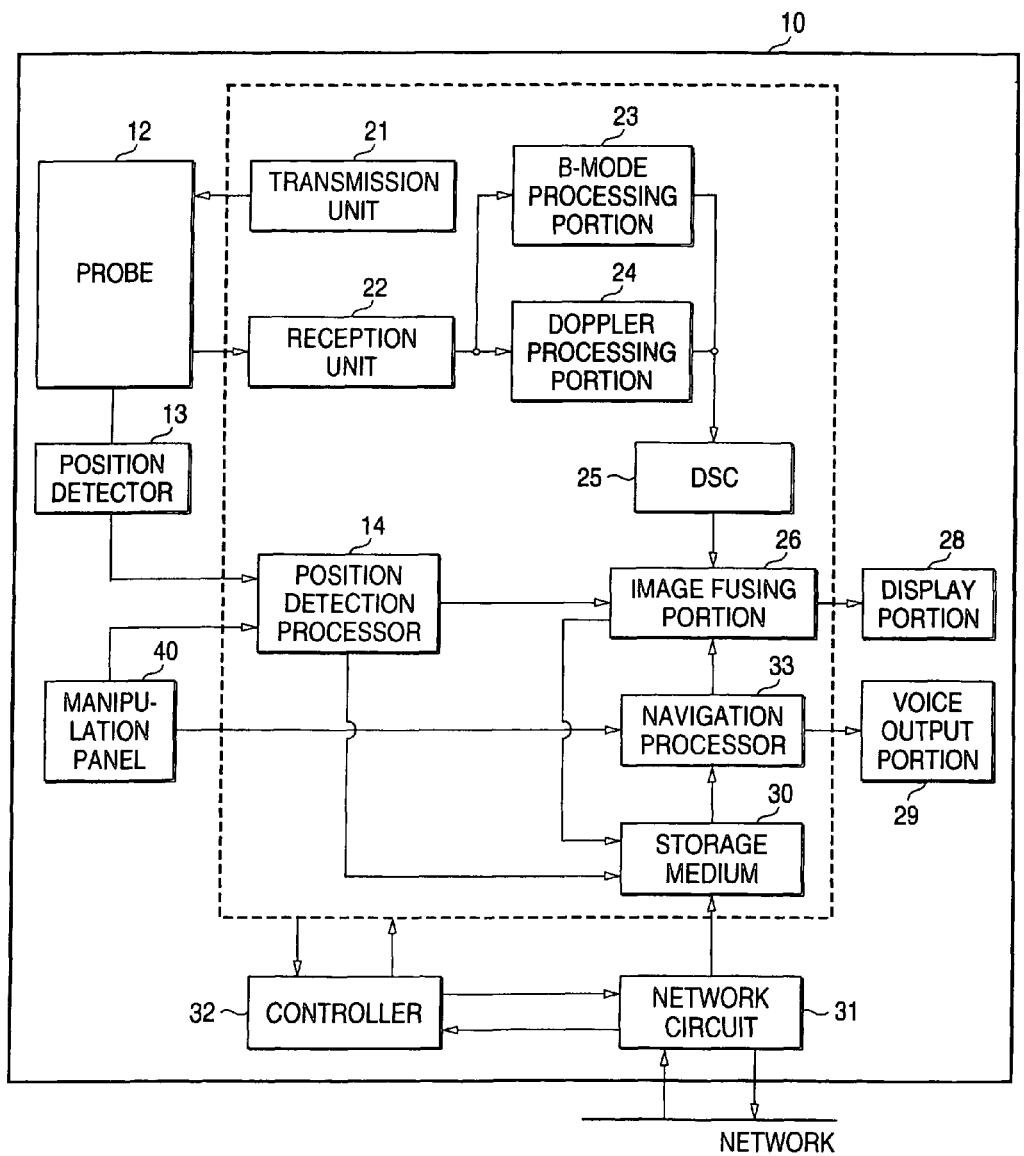
FIG. 1 is a block diagram schematically showing an arrangement of an ultrasonic diagnosis apparatus according to a first embodiment.

First through third embodiments of the invention will now be explained with reference to the accompanying drawing. Hereinafter, components having like functions and arrangements are labeled with like reference numerals and the explanation will not be repeated unless necessary.

(First Embodiment)

FIG. 1 is a block diagram schematically showing an arrangement of an ultrasonic diagnosis apparatus 10 according to a first embodiment. As shown in the drawing, the ultrasonic diagnosis apparatus 10 comprises an ultrasonic probe 12, a position detector 13, a position detection processor 14, an ultrasonic transmission unit 21, an ultrasonic reception unit 22, a B-mode processing portion 23, a Doppler processing portion 24, a DSC (Digital Scanner Converter) 25, an image fusing portion 26, a display portion 28, a voice output portion 29, a storage medium 30, a network circuit 31, a controller 32, a navigation processor 33, and a manipulation panel 40.

The ultrasonic probe 12 includes a plurality of piezoelectric transducers, which are in effect electroacoustic reversible transduction elements, such as piezoelectric ceramic. The piezoelectric transducers are aligned in parallel and installed at the tip of the ultrasonic probe 12. An arrangement of the ultrasonic probe 12 will be described in detail below.

The position detector 13 is installed inside the ultrasonic probe 12 or fixed to the ultrasonic probe 12 with an attachment or the like, and detects position information that specifies the position and the posture (orientation) of the ultrasonic probe 12. The position detector 13 is a sensor that detects a position based on, for example, a magnetic field, and it comprises at least two wired or wireless detectors to acquire position information on at least two points of the ultrasonic probe 12. More concretely, detectors known by the trade name Fastrack of Polhemus, Inc., Flock of Birds of Ascension Technology, Corp., etc. are available as the position detector 13. The position information detected by the position detector 13 is transmitted to the position detection processor 14 from time to time.

The position detection processor 14 specifies the position and the posture of the ultrasonic probe 12 (that is, a tilt with respect to a horizontal plane and a rotational angle about the central axis of the ultrasonic probe 12) based on the position information detected by the position detector 13. More specifically, the position detection processor 14 specifies the position and the posture of the ultrasonic probe 12 as described below.

Figure 2:
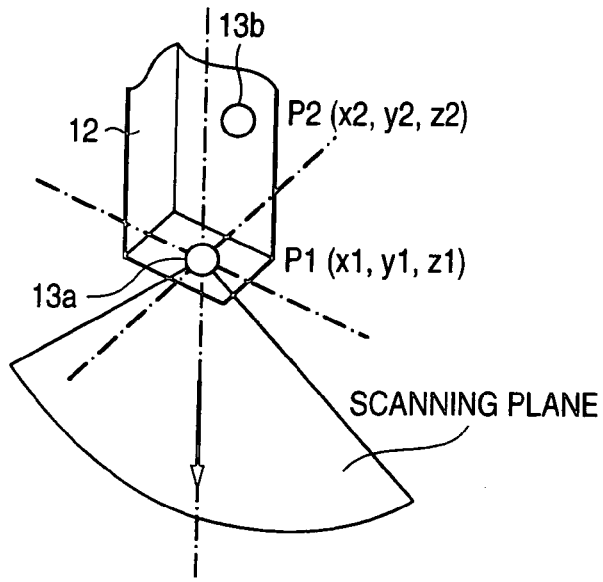
FIG. 2 is a view used to explain a method of specifying a position and a posture of an ultrasonic probe by a position detector and a position detection processor.

FIG. 2 is a view used to explain a method of specifying the position and the posture of the ultrasonic probe 12 by the position detector 13 and the position detection processor 14. As shown in the drawing, a position detector 13a and a position detector 13b are installed inside the ultrasonic probe 12 at two points in a configuration so as not to align along the central axis (an axis in a direction perpendicular to an ultrasound radiation plane indicated by an arrow in FIG. 2) of the ultrasonic probe 12.

The sensors 13a and 13b detect two points, a point P1 and a point P2, respectively. The position information on the point P1 and the point P2 is transmitted to the position detection processor 14 from time to time. The position detection processor 14 then detects the position of the ultrasonic probe 12 from the positions of the point P1 and the point P2, and detects the posture of the ultrasonic probe 12 from the relation between the point P1 and the point P2. To be more specific, the position detection processor 14 specifies a rotational angle (to what extent the ultrasonic probe 12 has rotated about the central axis) and a tilt (an angle with respect to a horizontal plane) from an angle between a straight line linking the centers of the position detector 13a and the position detector 13b and the central axis of the ultrasonic probe 12.

Although it is not shown in the drawing, the ultrasonic transmission unit 21 comprises a trigger generator, a delay circuit, and a pulsar circuit, and generates a pulsed driving signal. By supplying the driving signal from the ultrasonic transmission unit 21 to the ultrasonic probe 12, a focused ultrasonic pulse is transmitted toward a subject. Ultrasound thus transmitted is scattered by tissue inside the subject, received at the ultrasonic probe 12 again as echo signals, and taken into the ultrasonic reception unit 22.

Although it is not shown in the drawing, either, the ultrasonic reception unit 22 includes a preamplifier, an analog-to-digital converter, a reception delay circuit, and an adder. Each echo signal taken into the ultrasonic reception unit 22 is amplified in the preamplifier for each channel and subjected to analog-to-digital conversion, then given with a delay time needed to decide the reception directivity in the reception delay circuit, and added up in the adder. The addition enhances reflection components from a direction corresponding to the reception directivity. The transmission directivity and the reception directivity together generate signal strength data.

The B-mode processing portion 23 receives the echo signals processed in the ultrasonic reception unit 22. The B-mode processing portion 23 applies processing, such as logarithmic amplification and envelope detection, to input echo signals, and thereby generates a signal indicating the signal strength by brightness. A signal thus generated is sent to the DSC 25 and displayed on the display portion 28 as a B-mode image indicating the strength of a reflection wave by brightness.

The Doppler processing portion 24 extracts blood flow components (contrast medium echo components) by exploiting the Doppler effect, and finds blood flow information, such as an average velocity, variance, and power, at a number of points. The blood flow information is sent to the DSC 25, and displayed on the display portion 28 as an average velocity image, a variance image, a power image, or a combined image of the foregoing, all in color.

The DSC 25 converts a sequence of scan line signals specific to an ultrasonic scan to a sequence of scan line signals of a typical video format generally used for a TV or the like.

The image fusing portion 26 fuses a real-time image outputted from the DSC 25, character information or a scale of various setting parameters, and navigation information described below, and outputs a resulting video signal to the display portion 28. Also, the image fusing portion 26 selectively displays a reference image as the navigation information on the display portion 28 in response to a predetermined manipulation.

The display portion 28 is a CRT or the like that not only displays an ultrasonic image and the navigation information described below, but also functions as a console window when various analysis programs are executed.

The voice output portion 29 provides the operator with the navigation information in voice when a navigation system described below is run.

The storage medium 30 stores a pre-defined diagnosis analysis program, ultrasonic images acquired in the past to be used as reference images in a currently used or another ultrasonic diagnosis apparatus 10, the position information of the ultrasonic probe 12 when the respective ultrasonic images were acquired on a patient-by-patient basis. The storage medium 30 also stores libraries of diagnosis images (X-ray CT images, MR images, etc.) acquired in other modality used to generate a pseudo ultrasonic image described below, software programs needed to run the navigation system described below, voices and images, etc. The storage medium 30 can be, for example, a PROM (an EPROM, an EEPROM, a flash EPROM) and other IC memories, such as a DRAM, an SRAM, and an SDRAM, as well as an optical disc, a magnetic disc, a magneto-optical disc, a semiconductor device, etc. The data stored in the storage medium 30 can be transferred to an external peripheral apparatus over a wired or wireless network via the network circuit 31.

The network circuit 31 enables transmission and reception of various data with other apparatuses over a network, such as an in-hospital LAN, a WAN, and the Internet.

The controller 32 has the capability of operating as an information processing apparatus (computer), and controls operations of the ultrasonic diagnosis apparatus main body.

The navigation processor 33 runs the navigation system according to a predetermined program. The content of the navigation system will be described in detail below.

The manipulation panel 40 is a device connected to the ultrasonic diagnosis apparatus 10 and used to input command information from the operator. The manipulation panel 40 comprises buttons, a keyboard, a mouse, a track ball, a TCS (Touch Command Screen), etc., through the use of which the operator is able to control the ultrasonic diagnosis apparatus 10 and set various image quality conditions. The operator inputs a command to start/stop the navigation system described below, a command to take in a reference image, etc. through the manipulation panel 40.

<Navigation System>

The navigation system provided by the ultrasonic diagnosis apparatus 10 will now be explained. The navigation system provides the navigation information to assist manipulations of the ultrasonic diagnosis apparatus 10 in a user-friendly manner. The navigation system makes it easier for those who are less trained, such as a less experienced technician and a patient, to manipulate the ultrasonic diagnosis apparatus 10.

The navigation information includes reference images acquired by those who are well trained (for example, experienced physicians and technicians, etc.) to be referred to by those who are less trained, reference position information that is in effect the probe position information when the respective reference images were acquired, current probe position information, probe movement information indicating either or both a direction of movement and a quantity of movement of the ultrasonic probe 12 induced from the reference position information and the current probe position information, etc. The respective items of the information are displayed as the navigation information either selectively or concurrently as circumstances demand. It should be noted that these items of information included in the navigation information were given by way of example, and information of any other item may be included as well. For example, similarities between a currently picked-up ultrasonic image and a reference image may be computed and included in the navigation information.

Operations of the navigation system can be roughly divided into two. One includes operations to acquire a reference image and the reference position information, and the other includes operations to provide navigation information in diagnosis. Operations to acquire a reference image and the reference position information will be explained first, followed by operations to provide the navigation information.

Figure 3:
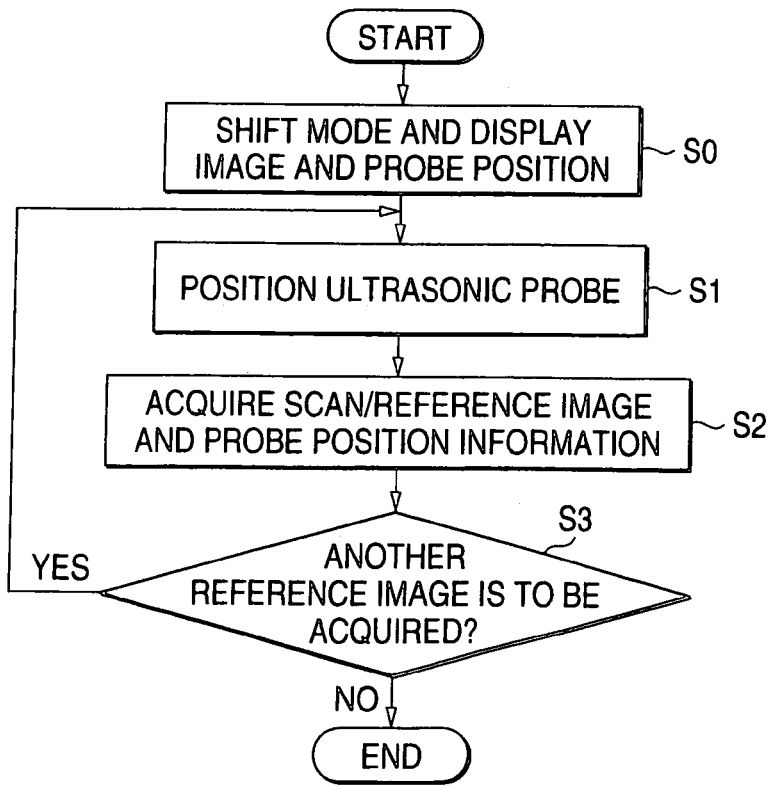
FIG. 3 is a flowchart detailing a flow when an experienced technician or the like acquires a reference image to be used as navigation information.
Figure 4:
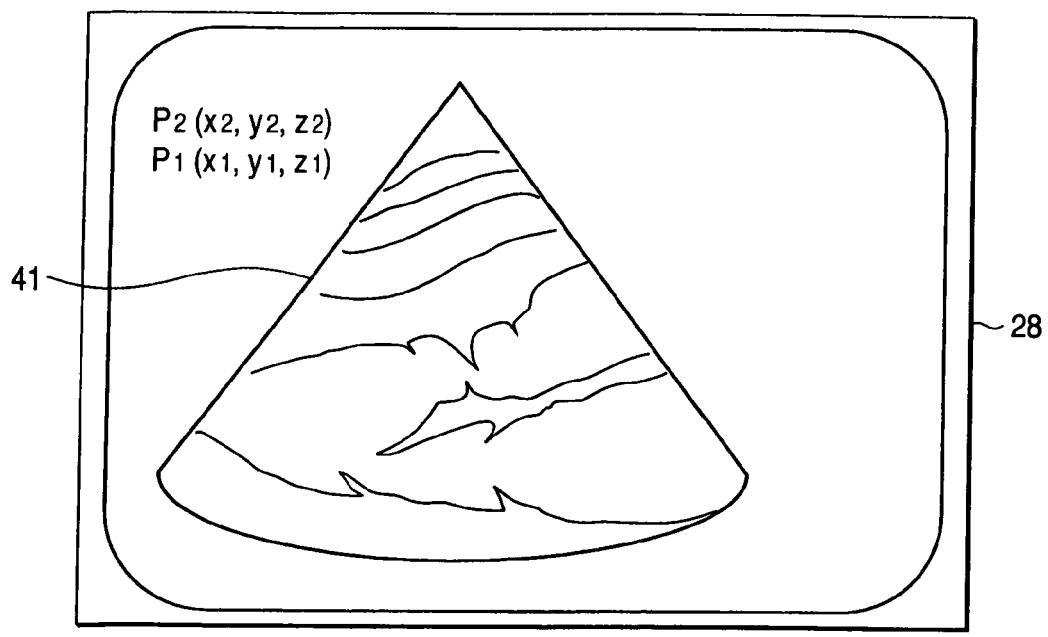
FIG. 4 is a view of a display screen on a display portion, showing a currently picked-up ultrasonic image and a current position of the ultrasonic probe.

FIG. 3 is a flowchart detailing a flow when an operator who is an experienced technician or the like acquires a reference image and the reference position information. The operator first shifts the mode to a reference image acquisition mode by a predetermined manipulation, and as shown in FIG. 4, allows an ultrasonic image acquired in real time and the current position information of the ultrasonic probe 12 to be displayed on the display portion 28 (Step S0).

Then, the operator positions the ultrasonic probe 12 to adequately acquire, for example, a long-axis tomographic image of the heart while watching an ultrasonic image displayed in real time (Step S1). Having positioned the ultrasonic probe 12, the operator presses a save button on the manipulation panel 40, in response to which a currently picked-up ultrasonic image is stored into the storage medium 30 as a reference image and the position of the ultrasonic probe 12 in this instance is stored as the reference position information (Step S2).

Then, when the operator wishes to acquire another reference image, for example, a reference image acquired by changing the position of the ultrasonic probe 12, he repeats processing in Step S2 and Step S3. When any other reference image is not needed, the operator ends the acquisition of a reference image (Step S3). A plurality of reference images acquired in this manner are eventually correlated with one another in the order of acquisition, and stored into the storage medium 30 as the navigation information as a whole.

Operations to provide the navigation information will now be explained. An explanation will be given to a case where, for example, a less experienced technician or the like acquires a plurality of long-axis tomographic images of the heart with reference to the navigation information provided in diagnosis.

Figure 5:
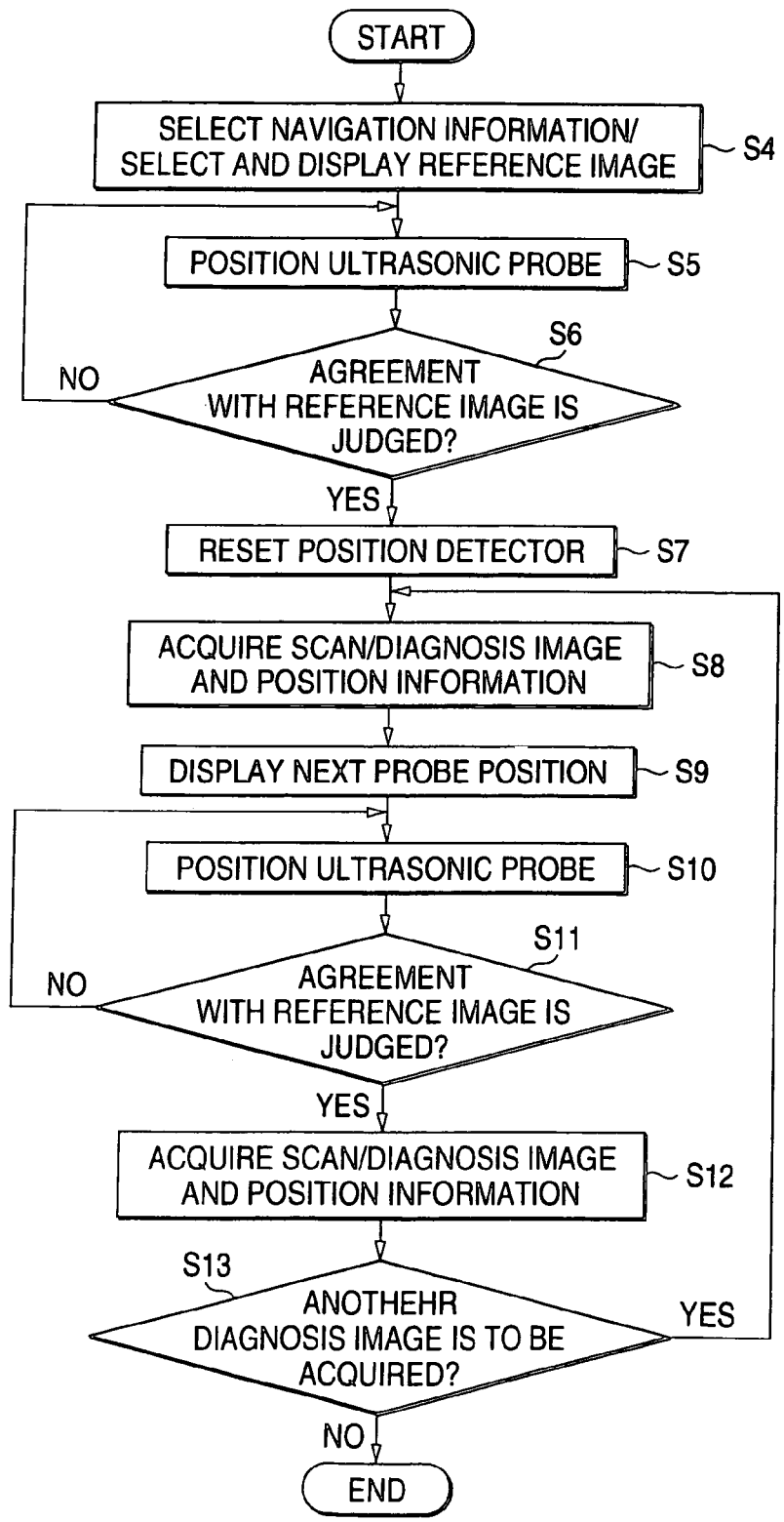
FIG. 5 is a flowchart used to explain operations of a navigation system according to the first embodiment.

FIG. 5 is a flowchart detailing a flow when the navigation system provides the navigation information. As shown in FIG. 5, the operator first inputs a command to run the navigation system, a command to select items of the navigation information to be used, etc. through the manipulation panel 40. Then, the navigation processor 33 reads out the selected items of the navigation information from the storage medium 30, and displays a first reference image on the display portion 28 (Step S4). In this case, the items of the navigation information to be read include a plurality of long-axis tomographic images of the heart as reference images and the corresponding reference position information. It should be noted that the plurality of long-axis tomographic images of the heart are those of the patient to be diagnosed.

Figure 6:
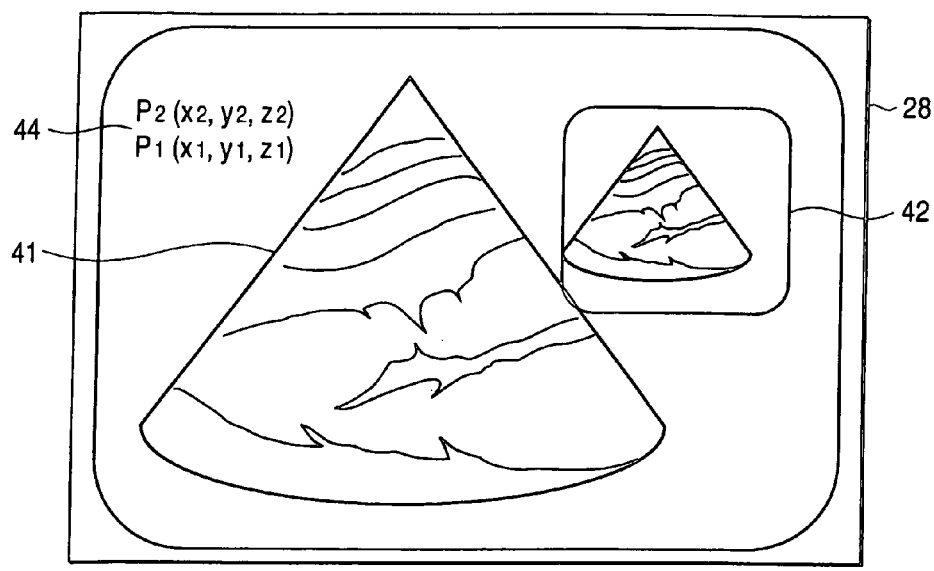
FIG. 6 is a view showing a display mode of a reference image on the display portion.

FIG. 6 is a view showing a display mode of a reference image on the display portion 28. As shown in the drawing, a reference image 42 is displayed together with an ultrasonic image 41 displayed in real time and current position information 44 of the ultrasonic probe 12.

Then, the operator positions the ultrasonic probe 12, by comparing a currently picked-up ultrasonic image with the reference image both being displayed, in acquiring an ultrasonic image identical to the reference image (Step S5). By pressing a reference-image refer button with the ultrasonic probe 12 being thus positioned, a judgment is made as to whether the currently picked-up ultrasonic image agrees with the reference image 42 both being displayed (Step S6). For such a judgment to be made, the navigation processor 33 finds similarities between the two images, for example, through image processing, image recognition, etc., and agreement is judged when the similarities reach or exceed a predetermined value. Alternatively, a reset operation in the following step may be performed at the instant the reference-image refer button is pressed without making such a judgment.

When agreement between a diagnosis image and the reference image is judged, a detected value in the position detector 13 is reset by a predetermined manipulation or automatically, and "0" is then given to the position information 44 of the ultrasonic probe 12 shown in FIG. 6 (Step S7). This resetting operation completes the alignment of the position between the ultrasonic probe 12 currently used and the ultrasonic probe 12 used when the reference image was acquired, based on the reference image and the currently acquired ultrasonic image. The position information 44 displayed on the display portion 28 after the resetting operation thereby indicates displacement from the position of the ultrasonic probe 12 when the reference image as a sample was acquired. The position information 44 therefore allows the operator to understand swiftly and quantitatively to what extent the ultrasonic probe 12 he is currently manipulating is displaced from the desired position (reference position information) of the ultrasonic probe 12. When disagreement between the diagnosis image and the reference image is judged in Step S6, the operator repetitively positions the ultrasonic probe 12 until agreement is judged.

After the ultrasonic probe 12 is positioned, a currently pick-up image is taken therefrom as a diagnosis image according to a predetermined manipulation, and stored into the storage medium 30 (Step S8). At the same time, the position information of the ultrasonic probe 12 detected by the position detector 13 is stored in correlation with the diagnosis image.

Subsequently, the operator moves ahead to the acquisition of the following diagnosis image. The navigation processor 33 displays, as the navigation information, a reference image used to acquire the following diagnosis image and the probe movement information indicating in what manner the ultrasonic probe 12 has to be moved to acquire the reference image, on the display portion 28 (Step S9). The probe movement information 46 can be calculated from the reference position information in relation to the reference image used to acquire the following diagnosis image and the position information of the ultrasonic probe 12 currently detected by the position detector 13.

Figure 7A:
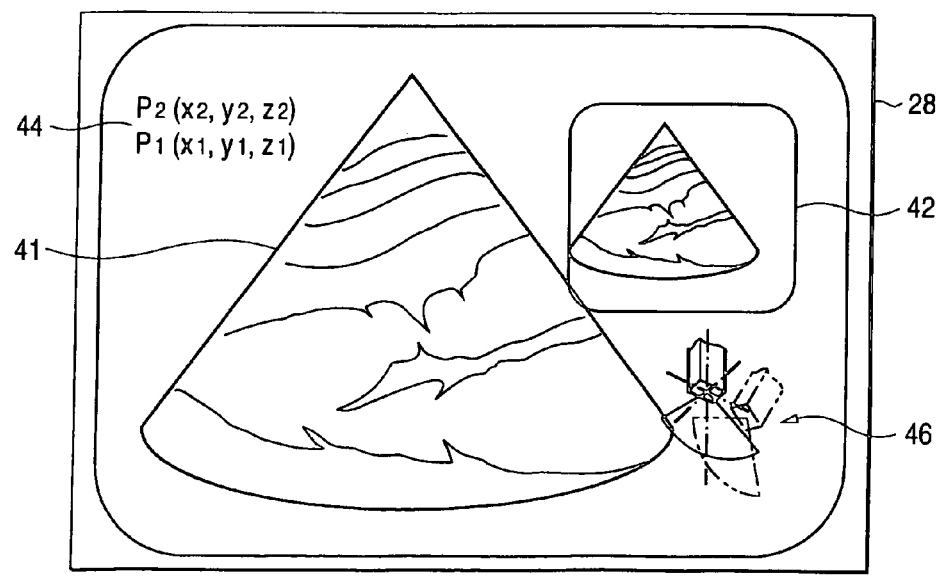
FIG. 7A is a view showing one example of a display mode of the navigation information.

FIG. 7A is a view showing a display example of the navigation information (reference image 42 and probe movement information 46) displayed when the operator moves to the acquisition of the following diagnosis image. The ultrasonic probe movement information 46 is displayed as a view showing the relation between the ultrasonic probe 12 at the current position and the ultrasonic probe 12 at the position at which the reference image can be acquired. The probe movement information 46 shown in the drawing comprises a probe A (solid line) indicating the current position and posture of the ultrasonic probe 12, and a probe B (dotted line) indicating the position and the posture to which the ultrasonic probe 12 has to be moved. The probe B is displayed as a still image at specific position and posture so that the probe A can be moved in association with a movement of the ultrasonic probe 12.

Then, the operator positions the ultrasonic probe 12 by controlling the position and the posture of the ultrasonic probe 12 so that the probe A displayed in a solid line superposes the probe B displayed in a dotted line while watching the probe movement information 46 (Step S10). In this instance, it is preferable that the positional relation between the probe A and the probe B is presented to the operator actively in a predetermined display mode, in which, for example, the probe A is displayed in color as it nears the probe B and flashed on and off upon agreement. By being provided with the navigation information as described above, even a less experienced technician or the like can readily understand the position to which the ultrasonic probe 12 has to be moved next.

It may be arranged in such a manner that the probe movement information 46 is provided in voice from the voice output portion 29. In this case, for example, a direction in and a distance over which the ultrasonic probe 12 has to be moved, a direction in and an angle at which the ultrasonic probe 12 has to be inclined, and a direction in and an angle at which the ultrasonic probe 12 has to be twisted are outputted in voice in guiding the operator to move the ultrasonic probe 12 to a position at which the reference image can be acquired.

Figure 7B:
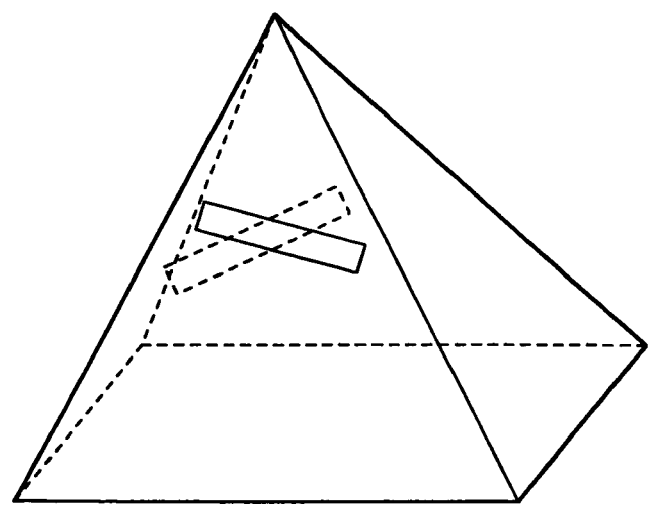
FIG. 7B is a view showing current probe position and posture and target probe position and posture in a representative manner.

It should be noted, however, that the display mode of the probe movement information 46 is not limited to the example of FIG. 7A, and can be of any arrangement as long as the similar contents are indicated. For example, as shown in FIG. 7B, it may be arranged in such a manner that an object representing spatial position and posture of the ultrasonic probe 12 may be displayed on the display portion 28 as the probe movement information 46. In the case of FIG. 7B, a solid line indicates the current probe position and posture and a dotted line indicates target probe position and posture in a representative manner.

Figure 7C:
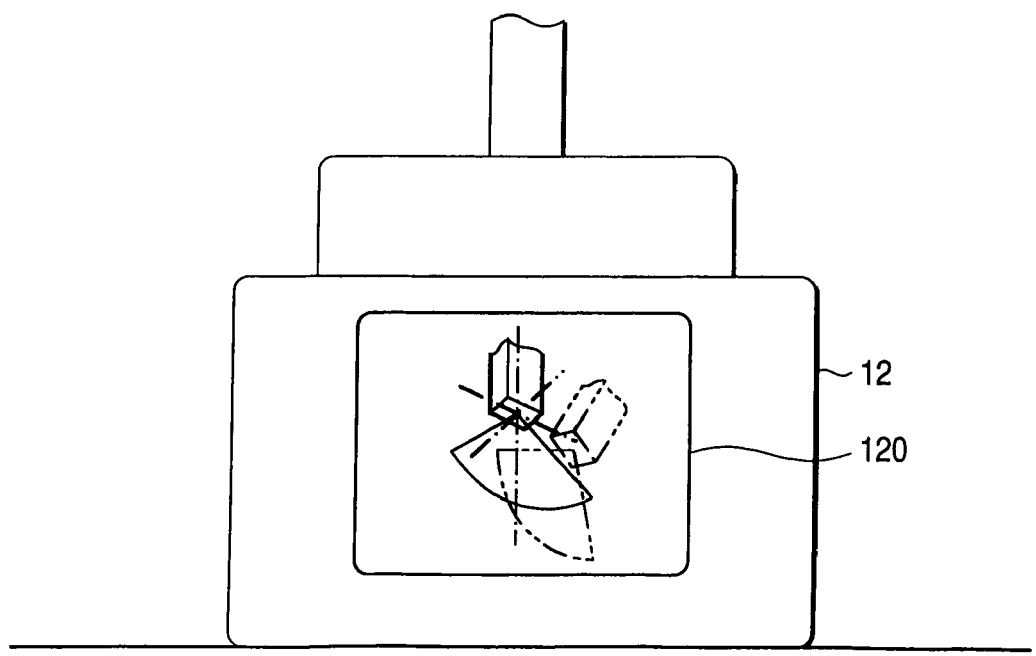
FIG. 7C is a view showing an ultrasonic probe provided with a display portion that displays probe movement information.

Alternatively, as shown in FIG. 7C, it may be arranged in such a manner that a display portion 120 is provided to the ultrasonic probe 12 to display the probe movement information 46 on the display unit 120. Further, it may be arranged in such a manner that the ultrasonic probe 12 is provide with a plurality of light emitting diodes indicating vertical and horizontal directions, so that a direction of movement and a quantity of movement are indicated by flashing on and off the light emitting diodes. This arrangement allows the operator to focus his attention to the ultrasonic probe 12. It is thus possible to provide an imaging system easy to use for those who are less skilled in imaging manipulations.

Then, the operator presses a reference-image refer button with the ultrasonic probe 12 being thus positioned, in response to which a judgment is made as to whether a currently picked-up ultrasonic image agrees with the reference image both being displayed (Step S11). When disagreement is judged, the operator repetitively positions the ultrasonic probe 12 until agreement is judged. On the other hand, when agreement is judged, the second diagnosis image is taken therefrom in response to a predetermined operation and stored into the storage medium 30 (Step S12).

Subsequently, when the operator wishes to acquire another diagnosis image, he repeats the processing from Step S9 through Step S12. When the operator wishes to end the acquisition of any other diagnosis image, for example, by having acquired diagnosis images as many as the prepared reference images, he ends the operation of the navigation system (Step S13).

It should be appreciated that in this navigation system, diagnosis images as many as all the prepared reference images are not necessarily acquired, and the operator may skip given reference images when deemed appropriate.

According to the arrangement described above, it is possible to provide the operator with reference images, the probe position information, etc. for him to refer to as the navigation information. The operator, by referring to the navigation information, becomes able to pick-up diagnosis images while understanding, for example, a difference and a correspondence between a reference image and a currently picked-up ultrasonic image. Hence, even when a less experienced technician or a patient picks up images, appropriate diagnosis images of a region to be diagnosed can be acquired.

Also, according to this navigation system, a quantity of displacement between the probe position at which the ultrasonic probe has to be present to acquire a reference image (reference position information) and the current probe position, and the position to and a direction in which the ultrasonic probe has to be moved to acquire the following diagnosis image are directed. Hence, even a less trained operator can understand quantitatively and concretely in what manner he has to operate the ultrasonic probe next, and is thereby able to perform imaging processing promptly.

Further, the navigation information can be received from a hub hospital or the like over a network via the network circuit 31 when necessary. Hence, a patient at a remote place or at home can pick up ultrasonic images according to the navigation information. The patient can therefore receive a high quality diagnosis based on suitable diagnosis images by transferring the ultrasonic images picked up appropriately according to the navigation information to a hub hospital or the like.

(Second Embodiment)

A second embodiment will describe a case where the navigation information is generated and provided based on images acquired in different modality (an X-ray CT apparatus, a magnetic resonance diagnosis apparatus, a nuclear medical diagnosis apparatus, etc.), for example, images of 3-D X-ray CT imaging, MRI, etc. This case is useful, for example, when CT images or the like outnumber ultrasonic images in the patient's image data in the past.

Figure 8:
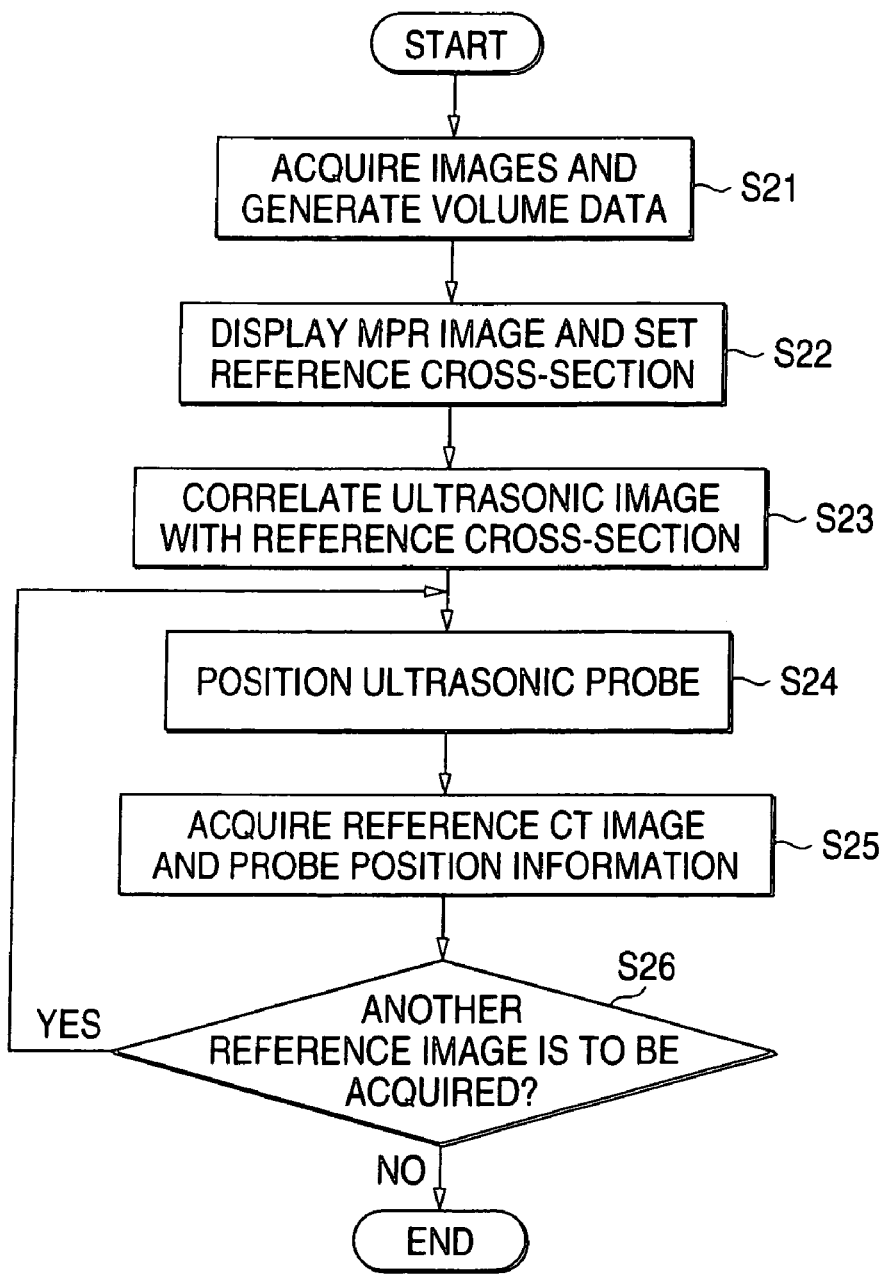
FIG. 8 is a flowchart used to explain operations of a navigation system according to a second embodiment.

FIG. 8 is a flowchart used to explain operations to acquire and generate reference images or the like in a navigation system according to the second embodiment. Referring to FIG. 8, diagnosis images are acquired and reconstructed first in other modality, for example, an X-ray CT apparatus, to generate volume data (Step S21).

Then, a reference cross-section is set in the volume data (Step S22). The reference cross section is set, for example, in the following manner. That is, a cross-sectional image is generated first from the volume data through the MPR (multi-plane reconstruction) method or the like. Then, the operator moves the position of the cross-sectional image to a desired position, and sets this particular cross-sectional image as a cross-sectional image used as the reference (reference cross-section). It is preferable that the image on the reference cross-section is of the same shape as an ultrasonic image, for example, a fan shape. Matching of the shapes can be achieved by a predetermined coordinate transformation.

Then, the reference cross-section is correlated with a currently picked-up ultrasonic image (position alignment) (Step S23). To be more specific, the operator, by moving the ultrasonic probe 12, adjusts the position of the currently picked-up ultrasonic image until a cross section identical to the reference cross-section is displayed. Then, the operator correlates the reference cross-section with the ultrasonic image (position alignment) by a predetermined manipulation, such as resetting, at the position where agreement is deemed. Once correlated with each other, the ultrasonic image and the MPR image are moved in association with a motion of the ultrasonic probe 12.

In order to achieve more accurate correlation, it may be arranged in such a manner that similarities between the two images are found through image recognition, image processing, etc., and two images are correlated with each other only when the similarities reach or exceed a threshold value.

Then, the operator positions the ultrasonic probe 12 to acquire the reference position information (Step S24). To be more specific, having been correlated with each other in Step S23, the ultrasonic image and the MPR image associated with a motion of the ultrasonic probe 12 are displayed on the display portion 28. The operator is thereby able to position the ultrasonic probe 12 to acquire the reference image by moving the ultrasonic probe 12 arbitrarily while referring to the two images moving in association.

Having positioned the ultrasonic probe 12 adequately, the operator presses a reference save button on the manipulation panel 40 with the ultrasonic probe 12 being thus positioned, in response to which the MPR image is acquired as a reference image (Step S25). When the reference save button is pressed, the navigation processor 33 stores the MPR image acquired in this instance into the storage medium 30 as the reference image. At the same time, the position information of the ultrasonic probe 12 detected by the position detector 13 is stored in correlation with the reference image. The positional relation between the reference image of the patient and the ultrasonic probe 12 is thus obtained. It may be arranged in such a manner that an ultrasonic image being picked up in this instance is also stored as a sub-reference image.

Subsequently, when the operator wishes to acquire another reference image, he repeats the processing in Step S24 and Step S25. On the other hand, when any other reference image is not needed, the operator ends the acquisition of a reference image (Step S26). A plurality of reference images thus acquired are eventually correlated with one another in the order of acquisition, and stored into the storage medium 30 as the navigation information as a whole.

The reference images or the like acquired through a series of processing described above are provided as the navigation information in diagnosis in the same manner as described in the first embodiment above (see FIG. 5).

According to the above arrangement, medical images acquired in other modality can be used as the navigation information, and therefore, the same advantages as those in the first embodiment above can be achieved. In addition, because the operator can position the ultrasonic probe while watching a CT image and an ultrasonic image concurrently, a reference image of a higher quality can be acquired. Further, because a reference image of a CT image and a reference image of an ultrasonic image can be acquired concurrently, work load during generation of reference images can be reduced.

(Third Embodiment)

A third embodiment describes a case where the navigation information is generated and provided based on images or the like acquired in different modality (an X-ray CT apparatus, a magnetic resonance diagnosis apparatus, a nuclear medical diagnosis apparatus, etc.). To be more specific, this embodiment describes a case where a reference image is generated from a CT image alone without being associated with an ultrasonic image in contrast to the second embodiment in which a CT image as a reference image is acquired with reference to an ultrasonic image and a CT image both associated with the ultrasonic probe.

FIG. 9 is a flowchart used to explain operations to acquire and generate reference images or the like in a navigation system according to the third embodiment. Referring to FIG. 9, diagnosis images are acquired and reconstructed first in other modality, for example, an X-ray CT apparatus, to generate volume data (Step S31).

Then, a 3-D position calculation is executed based on the position set by the operator, and a cross section (for example, an MPR image) set in a predetermined slice width or at an angular interval is set automatically at the corresponding position in the volume data (Step S32). The operator sets the position, for example, through the method of selecting a position from a plurality of pre-programmed positions, manually setting a cut plane in a model representing the volume data, etc.

Then, based on the cross section thus set, the position, at which the ultrasonic probe has to be placed when the cross section is deemed as an ultrasonic image, is estimated, and the image on the cross sections is stored as the reference image into the storage medium 30 and the estimated position of the ultrasonic probe is also stored as the reference position information (Step S33).

Further, when the operator wishes to acquire another reference image, he repeats the processing in Step S32 and Step S33. On the other hand, when any other reference image is not needed, the operator ends the acquisition of a reference image (Step S34). A plurality of reference images thus acquired are eventually correlated with one another in the order of acquisition, and stored into the storage medium 30 as the navigation information as a whole.

Diagnosis images or the like can be acquired according to the navigation information thus obtained in the same procedure as described in the first embodiment above (see FIG. 5).

According to the arrangement described above, images acquired in other modality can be used as the navigation information. It is thus possible to achieve an ultrasonic diagnosis apparatus, an ultrasonic probe, and an ultrasonic imaging assisting method that make manipulations easier and adequate for non-specialized or less experienced physicians or technicians, etc.

While embodiments of the invention have been described, it should be appreciated that anyone skilled in the art can achieve various modifications and adjustments, and it is understood that such modifications and adjustments are within the scope of the invention. For example, modifications as set forth in (1) and (2) below can be made without changing the gist of the invention.

(1) In each of the embodiments above, diagnosis images actually acquired from the subject are used as the reference images. However, the arrangement is not limited to the foregoing, and for example, animated images prepared in advance may be used as the reference images.

(2) In each of the embodiments above, the reference images, the reference position information, the current probe position information, displacement information of the current probe position, etc. were explained as examples of the navigation information. However, the navigation information is not limited to these items of information, and can be any information as long as it can be of any assistance for manipulations in diagnosis. For example, it may be arranged in such a manner that correctness as to manipulations of the probe may be actively presented to the operator by displaying quantitatively a judgment result on similarities between a reference image and an image being picked-up from time to time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnosis apparatus comprising:
an ultrasonic probe configured to transmit ultrasound to a subject and receive a reflection wave from the subject;
an image generator configured to generate a pick-up image based on the received reflection wave;
a memory configured to store a reference image obtained from an imaging modality other than an ultrasound imaging modality;
a determination unit configured to determine a similarity between the reference image and a currently imaging ultrasound image or a relation between a present position of the ultrasonic probe and a position where the ultrasonic probe is to be placed when a cross section is deemed as an ultrasonic image;
a navigation information generating unit configured to provide a user with navigation information helping the user to acquire an ultrasonic image at a position corresponding to that of the reference image on the basis of the similarity or the relation of the probe positions, the navigation information illustrating the probe at the present position and the probe at a position at which the reference image was acquired; and
a display unit which displays the navigation information, the currently imaging ultrasound image and the reference image at the same time, the reference image having a shape corresponding to the currently imaging ultrasound image.

2. The ultrasonic diagnosis apparatus of claim 1, further comprising a position detector configured to detect a position of the ultrasonic probe.

3. The ultrasonic diagnosis apparatus of claim 2, wherein the memory is further configured to store a reference position specifying a position of the ultrasonic probe in relation to the reference image.

4. The ultrasonic diagnosis apparatus of claim 3, further comprising an output unit configured to output the navigation information.

5. The ultrasonic diagnosis apparatus of claim 4, wherein the output unit is configured to display the pick-up image and the navigation information concurrently.

6. The ultrasonic diagnosis apparatus of claim 1, wherein the reference image has been acquired using an X-ray CT apparatus, the apparatus transforms the reference image and displays a transformed image on the display.

7. The ultrasonic diagnosis apparatus of claim 1, wherein the reference image has been acquired using a magnetic resonance diagnosis apparatus, the apparatus transforms the reference image and displays a transformed image on the display.

8. The ultrasonic diagnosis apparatus of claim 1, wherein the reference image has been acquired using a nuclear medical diagnosis apparatus, the apparatus transforms the reference image and displays a transformed image on the display.

9. The ultrasonic diagnosis apparatus of claim 5, wherein the reference image has been acquired using an X-ray CT apparatus, the apparatus transforms the reference image and displays a transformed image on the display.

10. The ultrasonic diagnosis apparatus of claim 5, wherein the reference image has been acquired using a magnetic resonance diagnosis apparatus, the apparatus transforms the reference image and displays a transformed image on the display.

11. The ultrasonic diagnosis apparatus of claim 5, wherein the reference image has been acquired using a nuclear medical diagnosis apparatus, the apparatus transforms the reference image and displays a transformed image on the display.

12. An ultrasonic diagnosis method comprising:
   transmitting ultrasound to a subject using an ultrasonic probe and receiving a reflection wave from the subject;
   generating a pick-up image based on the received reflection wave using an image generator;
   storing a reference image obtained from an imaging modality other than an ultrasound imaging modality;
   determining a similarity between the reference image and a currently imaging ultrasound image or a relation between a present position of the ultrasonic probe and a position where the ultrasonic probe is to be placed when a cross section is deemed as an ultrasonic image;
   generating navigation information helping a user to acquire an ultrasonic image at a position corresponding to that of the reference image on the basis of the similarity or the relation of the probe positions, the navigation information illustrating the probe at the present position and the probe at a position at which the reference image was acquired; and
   displaying the navigation information, the currently imaging ultrasound image and the reference image at the same time, the reference image having a shape corresponding to the currently imaging ultrasound image.

13. The ultrasonic diagnosis method of claim 12, further comprising:
   detecting a position of the ultrasonic probe using a position detector.

14. The ultrasonic diagnosis method of claim 13, further comprising:
   storing a reference position specifying a position of the ultrasonic probe in relation to the reference image; and
   displaying the pick-up image and the navigation information concurrently in an output unit.

15. The ultrasonic diagnosis method of claim 12, further comprising:
   transforming the reference image, having been acquired using an X-ray CT apparatus.

16. The ultrasonic diagnosis method of claim 12, further comprising:
   transforming the reference image, having been acquired using a magnetic resonance diagnosis apparatus.

17. The ultrasonic diagnosis method of claim 12, further comprising:
   transforming the reference image, having been acquired using a nuclear medical diagnosis apparatus.

18. The ultrasonic diagnosis method of claim 14, further comprising:
   transforming the reference image, having been acquired using an X-ray CT apparatus.

19. The ultrasonic diagnosis method of claim 14, further comprising:
   transforming the reference image, having been acquired using a magnetic resonance diagnosis apparatus.

20. The ultrasonic diagnosis method of claim 14, further comprising:
   transforming the reference image, having been acquired using a nuclear medical diagnosis apparatus.

* * * * *